United States Patent [19]

Tsuchihashi et al.

[11] Patent Number: 4,628,120
[45] Date of Patent: Dec. 9, 1986

[54] PREPARING METHOD OF OPTICALLY ACTIVE KETONES

[75] Inventors: Genichi Tsuchihashi, Tama; Keisuke Suzuki, Chigasaki, both of Japan

[73] Assignee: Toyo Stauffer Chemical Co., Ltd., Tokyo, Japan

[21] Appl. No.: 661,440

[22] Filed: Oct. 16, 1984

[30] Foreign Application Priority Data

Oct. 19, 1983 [JP] Japan ................................ 58-195487

[51] Int. Cl.⁴ ............................................. C07C 45/51
[52] U.S. Cl. ...................................... 568/322; 568/361; 568/404; 558/51; 549/473
[58] Field of Search ............... 568/404, 322, 301, 405; 260/456 R; 549/473

[56] References Cited

U.S. PATENT DOCUMENTS

| | | | |
|---|---|---|---|
| 2,042,224 | 5/1936 | Groll et al. | 568/405 |
| 3,235,602 | 2/1966 | Russell | 568/405 |
| 3,491,153 | 1/1970 | Lyness | 568/322 |
| 4,085,136 | 4/1978 | Tucker | 260/465 R |
| 4,128,584 | 12/1978 | Martel et al. | 260/456 R |

OTHER PUBLICATIONS

Suzuki et al, Tetrahedron Letters, vol. 25, pp. 1817–1820 (1984).
Suzuki et al, Tetrahedron Letters, vol. 24, pp. 4997–5000 (1983).

*Primary Examiner*—James H. Reamer
*Attorney, Agent, or Firm*—Oblon, Fisher, Spivak, McClelland & Maier

[57] ABSTRACT

A preparing method of optically active ketones given by a general formula

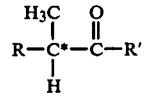

(wherein R represents a hydrocarbon group having 2 to 20 carbon atoms and R' represents a hydrocarbon group having 1 to 20 carbon atoms. The hydrocarbon groups of R and R' may contain functional groups having no influence on the reaction. But, * represents an asymmetric carbon atom, and R represents a more electron donating group than R' (except when R=R') through the rearrangement reaction by using organoaluminum compound.

19 Claims, No Drawings

PREPARING METHOD OF OPTICALLY ACTIVE KETONES

DETAILED DESCRIPTION OF THE INVENTION

The present invention relates to a novel preparing method of optically active ketones. In more detail, the invention relates to a novel preparing method of optically active ketones given by a general formula.

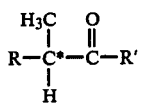

(wherein R represents a hydrocarbon group having 2 to 20 carbon atoms and R' represents a hydrocarbon group having 1 to 20 carbon atoms. The hydrocarbon groups of R and R' may contain functional groups having no influence on the reaction. But, * represents an asymmetric carbon atom, and R represents a more electron donating group than R' except when R=R' characterized by allowing optically active sulfonyloxy alcohols to subject to the pinacol rearrangement in the presence of organoaluminum compound.

Recently, an attempt for developing the insect pheromone as an agricultural chemical has been made actively. Both (+)-(S)-4-methyl-3-heptanone and (+)-(S)-4-methyl-3-hexanone, which are obtained through the hydrogenation of optically active ketones capable of preparing according to the invention, are the controlling substances of ant known as the alarm pheromones of ant. When used these for the expulsion of the ant, there is scarcely an influence on the human body and the environment since they are the natural substances. Moreover, the insect has an ability to distinguish the two enantiomers. Therefore, it is necessary to prepare ketones enantio-selectively.

The preparing method of these optically active ketones which are the alarm pheromones was in need of the resolution of the racemic modification hitherto which was multistage and/or time-consuming and uneconomical (Tetrahedron 30, 117, (1974) and Tetrahedron 33, 289 (1977)).

In order to improve the shortcoming described above, a method was proposed in Angewandte Chemie 91, 425 (1979) which can prepare the optically active ketones enantioselectively. However, this method needs many kind of reagents, and the final yield in synthesis of the objective substance from the starting substance is low. Moreover, this method uses ketones as the starting substances.

Furthermore, no methods for preparing the optically active ketones, in particular, acyclic ketones which uses alcohols as the starting substances are known yet. Generally, when allowing alcohols to subject the pinacol rearrangement, racemized ketones are obtained, even if the optically active alcohols are used. For example, when (R)-2-amino-1, 1-diphenyl-1-propanol is treated with nitrous acid, (R)-1,2-diphenyl-1-propanone is obtained at a racemization ratio of 24% (J. Am. Chem. Soc., 79, 6160 (1957).

In view of the situation described above, the inventors have diligently studied on a method capable of preparing ketones enantioselectively and easily using alcohols as the starting substances and, as a result, have reached the invention. Namely, the invention relates to a preparing method of optically active ketones given by the general formula.

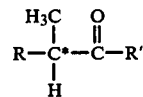

(wherein R, R¹ and * have the same definitions as above) characterized by allowing optically active sulfonyloxy alcohols given by a general formula.

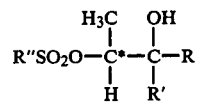

(wherein R represents a hydrocarbon group having 2 to 20 carbon atoms and R' represents a hydrocarbon group having 1 to 20 carbon atoms. The hydrocarbon groups of R and R' may contain functional groups having no influence on the reaction. R" represents a hydrocarbon group having 1 to 20 carbon atoms. But * represents an asymmetric carbon atom, and R represents a more electron donating group than R' (except when R=R')) to subject to the rearrangement reaction in the solvent and in the presence of organoaluminum compound.

In following, the invention will be explained concretely.

The optically active sulfonyloxy alcohols used in the invention are compounds given by the general formula.

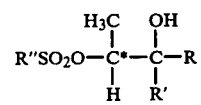

(wherein R, R', R" and * have the same definition as above) and are obtained by a publicly known method, for example, through the sulfonylation of the optically active vic-diols given by a general formula.

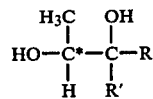

(wherein R, R' and * have the same definitions as above) with compounds given by a general formula R"SO₂Cl (wherein R" has the same definition as above), for example, mesyl chloride, tosyl chloride, etc. Here, as R , for example, vinyl, 1-propenyl, 1-butenyl, phenyl, phenylethyl, butyl, tolyl, methoxyphenyl, furyl, styryl, 1-pentenyl, etc. can be exemplified, and as R' methyl, ethyl, propyl, butyl, vinyl, allyl, amyl, 1-propenyl, phenyl, styryl, methoxyphenyl, tolyl, benzyl, phenylethyl, furyl, hexyl, octyl, decyl, etc. can be exemplified.

The optically active vic-diols described above can be synthesized, as shown in the referential examples, for example, when R=R', by allowing ethyl lactate to act with an excess of Grignard reagent, and when R≠R', by passing through amide.

The organoaluminum compounds used in the invention are those given by a general formula Rn"'AlX₃₋ₙ (wherein R''' represents a hydrocarbon group having 1 to 20 carbon atoms and X represents a hydrogen atom. n is a real number of 0 <n ≦3), and concretely, trimethylaluminum, triethylaluminum, tri-n-propylaluminum, triisopropylaluminum, tri-n-butylaluminum, triisobutylaluminum, tri-n-amylaluminum, triisoamylaluminum, tri-n-hexylaluminum, trioctylaluminum, tridecylaluminum, diethylaluminum hydride, diisobutylaluminum hydride, etc. can be exemplified. Preferable compound is trialkylaluminum, in particular, triethylaluminum.

Through allowing sulfonyloxy alcohols to subject to the rearrangement reaction for about 0.05 to 5 hours, preferably for 0.1 to 1 hour at room temperature to −80 C., preferably at 0 C. to −80 C. in the solvent and in the presence of organoaluminum compound, optically active ketones of the invention given by the general formula.

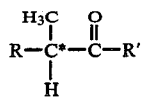

(wherein R, R' and * have the same definitions as above) are prepared.

As the solvents used for the rearrangement reaction described above, those which have no influence on the rearrangement reaction, for example, aliphatic hydrocarbons such as hexane, heptane, etc., aromatic hydrocarbons such as benzene, toluene, xylene, etc., alicyclic hydrocarbons such as cyclohexane etc., halogenated hydrocarbons such as dichloromethane, monochlorobenzene, etc. and others such as diethyl ether, tetrahydrofuran, anisol, etc. can be mentioned.

The amounts of organoaluminum compound to be used are 1 to 10 mol, preferably 1 to 5 mol for 1 mol of sulfonyloxy alcohol.

The amounts of solvent to be used are about 0.5 to 200 l, preferably about 1 to 50 l for 1 mol of sulfonyloxy alcohol.

The order of addition of sulfonyloxy alcohol, organoaluminum compound and solvent is arbitrary.

From the product of rearrangement reaction, objective optically active ketone can be refined and isolated by using known refining methods, for example, solvent extraction, filtration, distillation, chromatography treatment, etc. appropriately.

When the optically active ketones are prepared in accordance with the invention, objective substances, the absolute arrangement thereof being (S) or (R), can be obtained easily with an enantioselectivity of near 100% in high yield. Moreover, the method can use inexpensive lactic acid as a raw material. Based on these points, the invention has a great industrial value.

In following, the invention will be explained in more detail using referential examples and examples, but the invention is not confined to referential examples and examples described below.

REFERENCE EXAMPLE 1

Synthesis of (S)-,1-diphenyl-1,2-propanediol

Into anhydrous tetrahydrofuran (20 ml) was dissolved (S)-ethyl lactate (2.09 g, 17.7 mmol), and to this was added phenyl magnesium bromide (1.26 M tetrahydrofuran solution, 38 ml) under cooling with ice. After stirred for 1 hour under cooling with ice, phosphoric acid buffer solution (pH 7) was added to stop the reaction.

The product was extracted with ethyl acetate, and the extracted liquid was dried over anhydrous magnesium sulfate. Thereafter, oily residue obtained by concentrating under vacuum was refined and separated by the use of silica gel flash column chromatography (hexane/ethyl acetate=75/25) to obtain (S)-1,1-diphenyl-1,2-propanediol as white needle crystals (2.84 g, 70%).

IR(KBr-disk): 3580, 3510, 2900, 2830, 1490, 1445, 1270, 770, 755, 715, 700, 660 cm$^{-1}$.

NMR(CCl$_4$):δ=0.95 (d,J =6Hz, 3H), 2.9(S,1H), 3.0(S, 1H), 4.6(q,J =6Hz, 1H), 6.9-7.7(m, 10H). [α]$_D^{28}$−135° (C 3.075, C$_2$H$_5$OH).
m.p. 93.2–94.2° C.

REFERENCE EXAMPLE 2

Synthesis of 2-(S)-3,5-diphenyl-2,3-pentanediol

Into anhydrous tetrahydrofuran (20 ml) was dissolved (S)-1-0-(1-ethoxyethyl) lactic dimethylamide (3.82 g 20.1 mmol), and to this was added, β-phenylethyl magnesium bromide (0.52 M tetrahydrofuran solution, 46 ml) under cooling with ice. After stirred for 2 hours under cooling with ice, phosphoric acid buffer solution (pH 7) was added to stop the reaction.

The product was extracted wtih ethyl acetate, and the extracted liquid was dried over anhydrous magnesium sulfate. Thereafter, oily residue obtained by concentrating under vacuum was refined and separated by the use of silica gel flash column chromatography (hexane/ethyl acetate=95/5) to obtain 2-(S)-2-(1-ethoxyethyl)oxy-5-phenyl-3-pentanone as a pale yellow oily substance (4.70 g, 94%)

IR(Film): 3000, 2950, 2900, 1720, 1605, 1500, 1450, 1390, 1370, 1140, 1125, 1080, 1060, 1030, 955, 860, 760, 700 cm$^{-1}$.

NMR(CCl$_4$): δ=1.15 (d,j=6Hz, 3H), 1.20 (d,J=6Hz, 3H), 1.25 (t,J=4Hz, 3H), 2.5-3.0 (m, 4H), 3.1-3.7 (m,2H), 3.7-4.2 (m, 1H), 4.3-4.7 (m, 1H), 6.9-7.3 (m, 5H).

Into anhydrous tetrahydrofuran (3.5 ml) was dissolved 2-(S)-2-(1-ethoxyethyl)oxy-5-phenyl-3-pentanone (196 mg, 0.784 mmol), and to this was added phenyl magnesium bromide (0.64 M tetrahydrofuran solution, 2.4 ml) under cooling with ice. After stirred for 1 hour and a half under cooling with ice, phosphoric acid buffer solution (pH 7) was added to stop the reaction.

The product was extracted with ethyl acetate, and the extracted liquid was dried over anhydrous magnesium sulfate. Thereafter, oily residue obtained by concentrating under vacuum was dissolved into 8 ml of ethanol. To this was added pyridinium-p-toluene sulfonate (catalytic amount) and the mixture was stirred for 30 minutes at 40° C.

The oily residue obtained by concentrating the product under vacuum was refined and separated by the use of silica gel thin layer chromatography (hexane/ethyl acetate 7/3) to obtain 2-(S)-3,5-diphenyl-2,3-pentanediol as white needle crystals (145 mg, 72%).

IR(Film): 3500, 3440, 1500, 1450, 1270, 1260, 1090, 1070, 1010, 930, 880, 770, 750, 705 cm$^{-1}$.

MMR(CCl$_4$): δ=1.1 (d,J=6Hz, 3H), 1.7–2.3 (m, 2H), 2.0 (S, 1H), 2.3–3.0 (m, 2H), 2.6 (S, 1H), 3.6–4.1 (m, 1H), 6.7–7.5 (m, 10H).

REFERENTIAL EXAMPLE 3

Synthesis of (S)-2-methanesulfonyloxy-1,1-diphenyl-1-propanol

By treating (S)-1,1-diphenyl-1,2-propanediol with mesyl chloride, (S)-2-methanesulfonyloxy-1,1-diphenyl-1-propanol was obtained. Namely, as a result of the treatment of (S)-1,1-diphenyl-1,2-propanediol with $CH_3SO_2Cl$ (1.2 equivalent)-$(C_2H_5)_3$-N(1.5 equivalent) at 0° C. in $CH_2Cl_2$, (S)-2-methanesulfonyloxy-1,1-diphenyl-1-propanol was obtained in a yield of 87% (the position selectivity of this sulfonylation reaction was more than 95% from the measurement with $^1H$ NMR).

more than 99%. The specific rotation $[\alpha]_D^{25}$ was +200°(concentration 1.1 g/100 ml, $CHCl_3$) (value of $[\alpha]_D^{23}$ indicated in the literature is +202°(concentration 3.5 g/100 ml, $CHCl_3$) (J. Am. Chem. Soc., 74, 5846 (1952)) and the absolute arrangement was (S).

EXAMPLE 2-7

Employing vic-diols shown in Table 1, sulfonyloxy alcohols were prepared by the method in Referential example 3, and optically active ketones were synthesized by the same method as in Example 1. They were subjected to the analysis.

Results are shown in Table 1.

TABLE 1

| Example No. | Vic-diol R*[3] | R'*[3] | Temperature at rearrangement reaction (°C.) | Yield in*[1] synthesis (%) | enantiomeric excess (% ee) | Specific rotation*[2] $[\alpha]_D$ (Concn., Temp.) |
|---|---|---|---|---|---|---|
| 1 | $C_6H_5$— | $C_6H_5$— | −78 | 83 | >99 | +200° (1.1, 25) |
| 2 | p-$CH_3C_6H_4$— | p-$CH_3C_6H_4$— | −78 | 77 | >99 | +122° (0.74, 27) |
| 3 | $C_6H_5$— | $C_6H_5(CH_2)$— | −78 | 86 | >99 | +138° (0.42, 29) |
| 4 | p-$CH_3C_6H_4$— | $C_6H_5(CH_2)_2$— | −78 | 79 | >99 | +136° (0.92, 29) |
| 5 | p-$CH_3OC_6H_4$— | $C_6H_5(CH_2)_2$— | −78 | 96 | >99 | +141° (0.80, 26) |
| 6 | $H_2C=CH$— | $C_6H_5(CH_2)_2$— | −42 | 75 | >99 | +135° (0.34, 27) |
| 7 | 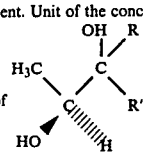 | $C_6H_5(CH_2)_2$— | −42 | 75 | >95 | +45° (0.50, 27) |

Notes
*[1]This indicates the yield of ketone from diol.
*[2]Measured using chloroform as a solvent. Unit of the concentration is g/100 ml

*[3]R and R' represent the substituents of $$\begin{array}{c} OH \quad R \\ H_3C \diagdown \ C \diagup \\ \diagup C \diagdown \\ HO \quad H \end{array}$$

EXAMPLE 1

(1) Synthesis of optically active ketone

To (S)-2-methanesulfonyloxy-1,1-diphenyl-1-propanol (153 mg, 0.5 mmol) present in 5 ml of $CH_2Cl_2$ in Referential example 3 was added a hexane solution of triethylaluminum (0.6 mmol, 0.7 ml) slowly at −78° C. The color of the solution changed to yellow. After stirred further for 30 minutes, the reaction was stopped with three drops of phosphate buffer solution having a pH value of 7. The suspension obtained was diluted with ethyl acetate, dried over anhydrous $Na_2SO_4$, filtered and concentrated. Oily residue was subjected to the chromatography treatment with Florisil column to obtain 1,2-diphenyl-1-propanone (100 mg, 96%).

(2) Analysis of optically active ketone systhesized

Through the reduction of ketone obtained in (1) with 1.5 equivalent of diisobutylaluminum hydride for 15 minutes at −78° C., 1,2-diphenylpropanol was obtained as a 5/1 diastereomer mixture. This was converted to the corresponding (+)-(α)-methoxy-α-trifluoromethyl-phenylacetic ester (hereinafter abbreviated to as (+)-MTPA ester) to obtain a sample.

Further, from ethyl lactate in racemic modification, 1,2-diphenyl-1-propanone in racemic modification was obtained by the same methods as Referential example 1 and 3 and aforementioned (1). This was converted similarly to (+)-MTPA ester to obtain a sample.

From the analysis of these two samples with HPLC and $^{19}F$ NMR, the enatiomeric excess of ketone obtained according to the invention was observed to be

EXAMPLE 8

To a solution of 524 mg (1.84 mmol) of 5-phenyl-3-(2-phenylethyl) pentane-2,3-diol dissolved into anhydrous methylene chloride (5ml) was added a solution of 378 mg (3.74 mmol) of triethylamine dissolved into anhydrous methylene chloride (2 ml) under cooling with ice, and further added a solution of 321 mg (2.80 mmol) of methanesulfonyl chloride dissolved into anhydrous methylene chloride (2 ml). After stirred for 1 hour and a half at 0° C., phosphoric acid buffer solution (pH 7) was added to stop the reaction.

The aqueous layer was extracted with ethyl acetate (10 ml×3 times), and the extracted liquid was washed in sequence with saturated aqueous solution of oxalic acid (10 ml×2 times), saturated salt solution (10 ml×1 time), 4% sodium bicarbonate solution (10 ml×2 times) and saturated salt solution (10 ml×1 time). After dried over anhydrous magnesium sulfate, the liquid was concentrated under vacuum to obtain 660 mg of 2-mesyloxy-5-phenyl-3-(2-phenylethyl)-3-pentanol as a pale yellow oily substance. Yield 99% (unrefined). IR(Film): 3550, 3045, 2955, 1604, 1498, 1454, 1329, 1174, 910, 754, 705 $cm^{-1}$ NMR($CCl_4$):δ=1.41 (3H,d,J=7 Hz), 1.52–2.05 (2H,m), 2.18 (1H, broad s), 2.30–2.90 (4H,m), 2.93 (3H,s), 4.78 (1H,q,J=7 Hz), 7.00–7.30 (10H,m).

To a solution of 86.0 mg (0.24 mmol) of 2-mesyloxy-5-phenyl-3-(2-phenylethyl)-3-pentanol (unrefined) dissolved into anhydrous methylene chloride (2.5 ml) was added 1.20 ml (1.20 mmol) of triethylaluminum (hexane 1M solution) at −78° C. under stirring. After stirred for 2 hours and a half at −78° C., the temperature was raised to 0° C. over a period of 3 hours. Several drops of phosphoric acid buffer solution (pH 7) were added to the reaction liquid, and then anhydrous sodium sulfate was added under stirring. The precipitates were filtered off using celite, and the residue was washed with ethyl acetate (10 ml×4 times). The filtrate and the washed liquid were combined and concentrated under vacuum. Oily product obtained was refined and separated by the use of thin layer silica gel chromatography (hexane/ethyl acetate 12/1) to obtain 30.0 mg of 1,6-diphenyl-4-methylhexane-3-one as a colorless oily substance. Yield 48%.

IR(Film): 3033, 2940, 2860, 1711, 1604, 1580, 1496, 1451, 1470, 1376, 750, 700 cm$^{-1}$.

NMR(CCl$_4$): δ=1.01 (3H,d,J=8 Hz), 1.16–2.23 (2H,m), 2.27–2.93 (7H,m), 6.95–7.30 (10H,m).

What is claimed is:

1. In a Pinacol-type rearrangement, the improvement comprising:

contacting an optically active sulfonyloxy alcohol of the formula:

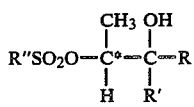

wherein R is a C$_2$ to C$_{20}$ hydrocarbon group, R' is a C$_1$ to C$_{20}$ hydrocarbon group, R" is a C$_1$ to C$_{20}$ hydrocarbon group, and * represents an asymmetric center, and wherein R is more electron donative than R' except when R and R' are identical, with an organoaluminum compound of the formula R$_n$'''AlX$_{3-n}$, wherein R''' is a C$_1$ to C$_{20}$ hydrocarbon group, X is a hydrogen atom, and 0<n≦3, to obtain an optically active ketone of the formula

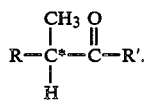

2. The Pinacol-type rearrangement of claim 1, wherein the said organoaluminum compound is a trialkylaluminum compound or a dialkylaluminum hydride compound.

3. The Pinacol-type rearrangement of claim 1, wherein the said organoaluminum compound comprises trimethylaluminum, triethylaluminum, tri-n-propylaluminum, tri-iso-propylaluminum, tri-n-butylaluminum, tri-iso-butylaluminum, tri-n-amylaluminum, tri-iso-amylaluminum, tri-n-hexylaluminum, trioctylaluminum, tridecylaluminum di-ethylaluminum hydride or di-iso-butylaluminum hydride.

4. The Pinacol-type rearrangement of claim 1, wherein the said organoaluminum compound is triethylaluminum.

5. The Pinacol-type rearrangement of claim 1, wherein the said rearrangement reaction is conducted at a temperature of from room temperature to −80° C.

6. The Pinacol-type rearrangement of claim 5, wherein the said rearrangement reaction is conducted at a temperature of from 0° C. to −80° C.

7. The Pinacol-type rearrangement of claim 1, wherein R" comprises methyl or para-tolyl.

8. The Pinacol-type rearrangement of claim 1, wherein R comprises vinyl, 1-propenyl, 1-butenyl, phenyl, phenylethyl, butyl, tolyl, methoxyphenyl, furyl, sytryl or 1-pentenyl.

9. The Pinacol-type rearrangement of claim 1, wherein R' comprises methyl, ethyl, propyl, butyl, vinyl, allyl, amyl, 1-propenyl, phenyl, styryl, methoxyphenyl, tolyl, benzyl, phenylethyl, furyl, hexyl, octyl, or decyl.

10. The Pinacol-type rearrangement of claim 1, wherein the said rearrangement reaction is run for a period of time from 0.05 to 5 hours.

11. The Pinacol-type rearrangement of claim 10, wherein the said time is from 0.1 to 1 hour.

12. The Pinacol-type rearrangement of claim 1, wherein the said rearrangement is run in a solvent comprising an aliphatic hydrocarbon, an aromatic hydrocarbon, an alicyclic hydrocarbon, a halogenated hydrocarbon an ether or anisol.

13. The Pinacol-type rearrangement of claim 12, wherein the said solvent comprises hexane, heptane, benzene, toluene, xylene, cyclohexane, dichloromethane, monochlorobenzene, diethylether or tetrahydrofuran.

14. The Pinacol-type rearrangement of claim 1, wherein the said organoaluminum compound is used in a 1 to 10 molar ratio relative to the said sulfonyloxy alcohol.

15. The Pinacol-type rearrangement of claim 14, wherein the said molar ratio is 1 to 5 mole.

16. The Pinacol-type rearrangement of claim 1, wherein a solvent is used in amount of from 0.5 to 200 liters per mole of sulfonyloxy alcohol.

17. The Pinacol-type arrangement of claim 16, wherein the said solvent is used in an amount of from 1 to 50 liters per mole of sulfonyloxy alcohol.

18. The Pinacol-type rearrangement of claim 1, wherein an optically active ketone having a (S) configuration is obtained.

19. The Pinacol-type rearrangement of claim 1, wherein an optically active ketone having a (R) configuration is obtained.

* * * * *